United States Patent
Ishii et al.

(10) Patent No.: US 6,387,359 B1
(45) Date of Patent: *May 14, 2002

(54) NONIONIC SURFACTANT

(75) Inventors: Hiroji Ishii; Masako Koyama, both of Kawasaki; Tomomichi Ichikawa, Tokyo; Toshihiko Funakubo, Sayama, all of (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,611

(22) Filed: Oct. 28, 1998

(30) Foreign Application Priority Data

Oct. 30, 1997 (JP) ................................ 9-334738

(51) Int. Cl.[7] .............................. A61K 7/06; A61K 7/04; A61K 7/021; A61K 7/15; A61K 38/00
(52) U.S. Cl. ........................... 424/70.1; 424/61; 424/63; 424/73; 514/12; 514/13; 514/17; 514/772.4; 514/723
(58) Field of Search .............................. 424/70.1, 70.31, 424/473, 61, 63, 73; 514/12, 13, 17, 723, 772.4

(56) References Cited

U.S. PATENT DOCUMENTS 5,466,396 A * 11/1995 Madison et al. ............. 252/557
5,744,062 A * 4/1998 Dahms et al. ............... 252/312

FOREIGN PATENT DOCUMENTS

| GB | 2140297 | 11/1994 |
|---|---|---|
| JP | 50 105580 | 8/1975 |
| JP | 54-62991 | 5/1979 |
| JP | 54 037839 | 5/1979 |
| JP | 54 062991 | 7/1979 |

* cited by examiner

*Primary Examiner*—Thurman K. Page
*Assistant Examiner*—S. Tran
(74) *Attorney, Agent, or Firm*—Oblon, Spivak, McClelland, Maier & Neustadt, P.C.

(57) ABSTRACT

Herein are disclosed N-long chain acyl-neutral amino acid polyglycerin esters composed of a polyglycerin having a degree of glycerin polymerization of not smaller than 4 and an N-long chain acyl-neutral amino acid having an acyl group with from 6 to 22 carbon atoms and a nonionic surfactant composition comprising, as an active ingredient, at least one of said N-long chain acyl-neutral amino acid polyglycerin esters, which are favorably safe and which, when incorporated in cosmetic compositions or percutaneous preparations, are sensorially good.

6 Claims, No Drawings

NONIONIC SURFACTANT

FIELD OF THE INVENTION

The present invention relates to an acyl-neutral amino acid polyglycerin ester, and more perticularly to an N-long chain acyl-neutral amino acid polyglycerin ester in which at least one or more N-long chain acyl-neutral amino acid molecules are bonded via ester bonding to one molecule of polyglycerin having a degree of glycerin polymerization of 4 or more, and to a nonionic surfactant composition comprising, as an active ingredient, at least one kind of such esters and a cosmetic composition or a percutaneous preparation comprising, as a nonionic surfactant ingredient, at least one kind of such esters in an effective amount.

Incidentally, the acyl-neutral amino acid polyglycerin ester is, as can be seen from its structural formula given later, a nonionic compound, and shows surface activity (emulsifying activity). For these reasons it is a kind of nonionic surfactant.

BACKGROUND OF THE INVENTION

Heretofore, anionic surfactants as used in soap emulsification in the past have been generally used as surfactants in producing emulsified products such as cosmetic compositions, percutaneous preparations, and the like, but, recently, ethylene oxide-based nonionic surfactants have become used popularly for that purpose. However, the safety of ethylene oxide-based nonionic surfactants is considered problematic in that they often irritate sensitive skins. Many consumers who take an increasing interest in the safety of products therefore desire ethylene oxide-free nonionic surfactants. In particular, they desire products of natural materials.

As nonionic surfactants which are less irritative or the like, and therefore highly safe are widely known polyglycerin fatty acid esters which are esterified products of polyglycerins with fatty acids.

As is well known, fatty acids are natural substances, and polyglycerins are condensation products of glycerin which is also a natural substance. Polyglycerin fatty acid esters are preferred to ethylene oxide-based nonionic surfactants in view of their safety, and the former can be produced easily on an industrial scale. However, conventional polyglycerin fatty acid esters cannot, when used in cosmetic compositions such as milky lotion, cream and the like or in percutaneous preparations, be always sensorially satisfactory, as they are often sticky or the like.

On the other hand, as less irritative and highly safe natural surfactants are widely used N-long chain acyl-neutral amino acids which are acylated products of amino acids with fatty acids. Some compounds wherein such N-long chain acyl-neutral amino acids are introduced, are known as nonionic surfactants usable as emulsifiers, etc. For example, in Japanese Patent Publication (kokoku) No. 62991/1979, it is disclosed that alcohol esters of N-long chain acyl-neutral amino acids are favorable as surfactants in the Perfume and cosmetic field. Alcohols referred to therein include polyalcohols, polyoxyalkylene-polyalcohols, etc. For example, mono(N-lauroyl-N-methyl-β-alanine) glycerin ester, di(N-lauroyl-N-methyl-β-alanine) glycerin ester and others described in the examples in the patent publication are among those N-long chain acyl-neutral amino acid glycerin esters noted above, and their safety is good.

Though having good safety, however, those monoglycerin and diglycerin esters are still problematic in that, when used in cosmetic compositions or percutaneous preparations, they can not be always satisfactory for the sensorial feel. For example, in actual use of such cosmetic compositions or percutaneous preparations comprising such esters, they are poorly spread on the skin and they are not smooth and are poorly compatible with the skin while giving little refreshing feel when they are applied to the skin, whereas they are often sticky and give little refreshing feel, after they have been applied to the skin.

In that situation of the prior art, now are desired nonionic surfactants which can be more excellent emulsifier and are safer and which, when incorporated into cosmetic compositions or percutaneous preparations, can provide sensorially satisfactory compositions or preparations.

SUMMARY OF THE INVENTION

The object of the present invention is to provide nonionic surfactants which are safer than conventional ones and which feel good in their use.

Given that situation noted above, the present inventors have assiduously studied and, as a result, have found that, when an N-long chain acyl-neutral amino acid polyglycerin ester composed of a polyglycerin having a degree of polymerization of not smaller than 4 and an N-long chain acyl-neutral amino acid having a long chain acyl group with from 6 to 22 carbon atoms is used as an emulsifier or the like in cosmetic compositions or percutaneous preparations, its gives a good feel in use of those cosmetic compositions or percutaneous preparations. On the basis of these findings, they have completed the present invention.

Specifically, the invention relates to an N-long chain acyl-neutral amino acid polyglycerin ester, which is composed of a polyglycerin having a degree of glycerin polymerization of not smaller than 4 and an N-long chain acyl-neutral amino acid having an acyl group with from 6 to 22 carbon atoms, and which is represented by the following general formula (I):

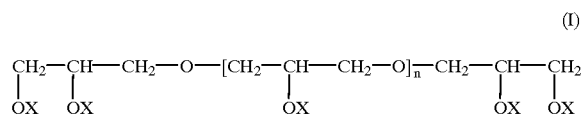

(I)

wherein at least one of plural X's represents an N-long chain acyl-neutral amino acid residue, and the remaining X's each independently represent a hydrogen atom or an N-long chain acyl-neutral amino acid residue, and n represents an integer of not smaller than 2, and wherein the acyl group in each N-long chain acyl-neutral amino acid residue is a straight-chain or branched-chain and saturated or unsaturated acyl group having from 6 to 22 carbon atoms.

The present invention relates also to a nonionic sufactant composition comprising, as an active ingredient, at least one kind of such N-long chain acyl-neutral amino acid polyglycerin ester in an effective amount as well as to a cosmetic composition and a percutaneous preparation comprising, as a nonionic surfactant ingredient, at least one kind of such N-long chain acyl-neutral amino acid polyglycerin ester in an effective amount.

DETAILED DESCRIPTION OF THE INVENTION

The invention will be described in detail hereinunder.

The long chain acyl group in the N-long chain acyl-neutral amino acid polyglycerin ester of the present invention is a straight-chain or branched-chain, saturated or unsaturated one having from 6 to 22 carbon atoms. As preferred examples of the acyl group may be mentioned acyl groups derivable from capric acid, lauric acid, myristic acid, palmitic acid, stearic acid, behenic acid, linolic acid, linolenic acid, oleic acid, isostearic acid, 2-ethylhexanoic acid, coconut oil fatty acids, beef tallow fatty acids, hardened beef tallow fatty acids, etc.

The neutral amino acid (residue) is not specifically limited, and includes, for example, glycine, alanine, valine, leucine, isoleucine, serine, threonine, proline, β-alanine, aminobutyric acid, sarcosine, N-methyl-β-alanine, etc. Especially preferred are glycine, alanine, β-alanine, aminobutyric acid, sarcosine and N-methyl-β-alanine.

The polyglycerin should have a degree of glycerin polymerization of not smaller than 4, and preferably from 4 to 10. Polyglycerins having a degree of glycerin polymerization of 3 or less are undesirable, since their esters could not give a good sensual feel.

One or more molecules of the N-long chain acyl-neutral amino acid may be introduced into one molecule of the polyglycerin via ester bonding. For example, tetraglycerin has 6 esterifiable hydroxyl groups in one molecule, in which a part or all of those hydroxyl groups may be esterified with the N-long chain acyl-neutral amino acid. Various types of nonionic surfactants having different HLB (hydrophile-lipophile balance) values can be produced, for example, by properly varying the degree of polymerization of the polyglycerin to be modified and also the number of molecules of the acyl-neutral amino acid to be bonded thereto, in accordance with the intended use.

The N-long chain acyl-neutral amino acid polyglycerin esters of the invention can be produced, for example, by heat-esterifying an N-long chain acyl-neutral amino acid with a polyglycerin under normal or reduced pressure for dehydration condensation (see Example 22 and others mentioned hereinunder). They may be also produced through azeotropic dehydration condensation reaction or transesterification reaction (see Example 1 and others mentioned hereinunder). It is also possible to addition-react glycidol or epichlorohydrin with an N-long chain acyl-neutral amino acid or N-long chain acyl-neutral amino acid glycerin ester to produce the N-long chain acyl-neutral amino acid polyglycerin esters of the present invention. Crude N-long chain acyl-neutral amino acid polyglycerin ester thus produced can be purified by steam-deodorizing, decolorizing with the use of an adsorbent such as activated carbon, desalting by washing with water or an aqueous inorganic salt solution, removing such impurities as unreacted polyglycerin, acylamino acid and the like with the use of an organic solvent such as hexane, or the like.

The N-long chain acyl-neutral amino acids and their glycerin esters to be used for producing such N-long chain glycidol, epichlorohydrin or the like. Commercially-available polyglycerins may be used according to the present invention, which include, for example, "Polyglycerin #310" (tetraglycerin), "Polyglycerin #500" (hexaglycerin), "Polyglycerin #750" (decaglycerin), all the products being ex Sakamoto Pharmaceutical Industry Co., etc.

In general, a polyglycerin product produced in those methods noted above are not composed of a single molecular species. For example, as for a tetraglycerin product, it often contains triglycerin, pentaglycerin and any other polyglycerins, and even non-reacted, starting glycerin. The polyglycerins thus produced may be purified to remove the other not-intended polyglycerins and the non-reacted glycerin therefrom, prior to being reacted with N-long chain acyl-neutral amino acids. If possible, however, they may be directly reacted with N-long chain acyl-neutral amino acids without being specifically purified.

An N-long chain acyl-neutral amino acid polyglycerin ester product of the present invention produced from an N-long chain acyl-neutral amino acid and a polyglycerin according to the methods mentioned above is usually in the form of a mixture of the intended ester and esterified polyglycerin compounds of which the degree of polymerization differs from the intended one, where the starting polyglycerins are not specifically purified prior to being reacted with the acids. However, for acyl-neutral amino acid polyglycerin esters are not always needed to be single compounds but may be in the form of mixtures of two or more of them that differ in the type of the acyl group therein and/or in the type of the neutral amino acid moiety therein. In such case, N-long chain acyl-neutral amino acid polyglycerin ester thus produced is one where a plurality of N-long chain acyl-neutral amino acids are different from one another when a pourality of X's represent a plurality of different N-long chain acyl-neutral amino acid residuces in the general structural formula (I) above. Further, an N-long chain acyl-neutral amino acid polyglycerin ester product thus produced is one composed of a mixture of a plurality of different molecular species, not of a single molecular species. In this sense, such mixture of N-long chain acyl-neutral amino acid polyglycerin esters can be called an nonionic surfactant "composition."

In this connection, N-long chain acyl-neutral amino acids may be produced in any known method of, for example, so-called Schotten-Baumann reaction wherein a long-chain fatty acid halide is reacted with an amino acid in the presence of a basic catalyst (see Japanese Patent Publication (*kokoku*) No. 38681/1976, etc.).

The polyglycerins may be produced also in any known method of, for example, dehydration condensation reaction of glycerin, or polymerization reaction of glycerin analogues such as use in the cosmetic compositions and the percutaneous preparation of the present invention, the polyglycerin esters are not always needed to have a single degree of polymerization. Even such a mixture of different types of polyglycerin esters that differ in the degree of polymerization of the polyglycerin moiety therein, shows of course the nonionic surfactant activity the N-long chain acyl-neutral amino acid polyglycerin ester of the present invention shows. Therefore, such mixture is also included in the nonionic surfactant composition of the present invention. In addition, the N-long chain acyl-neutral amino acid polyglycerin ester of the present invention may be in the form of a mixture with any of monoglycerin esters, diglycerin esters and triglycerin esters of N-long chain acyl-neutral amino acids within the range not interfering with the nonionic surfactant activity thereof, and such mixture is also included in the scope of the nonionic surfactant composition of the present invention.

One or more kinds of the N-long chain acyl-neutral amino acid polyglycerin esters of the present invention can be used as an emulsifier (nonionic surfactant) in formulating cosmetic compositions and percutaneous preparations, such as face wash cream, face wash foam, cleansing cream, massage cream, cold cream, moisturizing cream, milky lotion, lotion, hand cream, pack, skin cosmetics for men, skin-protecting agents for babies, foundation, lipstick, press powder, eye shadow, stick-form hair vegetable-derived oily substances such as macadamia nut oil, jojoba oil, carnauba wax, sesame oil, cacao butter, palm oil, mink oil, haze wax, candelilla wax, whale oil, etc., petroleum and mineral-derived oily substances such as paraffins, microcrystalline wax, liquid paraffin, vaseline, ceresine, etc., as well as silicones such as methylpolysiloxane, polyoxyethylene-methylpolysiloxane, polyoxypropylene-methylpolysiloxane, poly(oxyethylene-oxypropylene)-methylpolysiloxane, methylphenylpolysiloxane, fatty acid-modified polysiloxanes, aliphatic alcohol-modified polysiloxanes, amino acid-modified polysiloxanes and other silicone polymers; resin acids, esters, ketones, etc.

The cosmetic compositions and the percutaneous preparations of the present invention may also optionally contain, any other various surfactants within the range not interfering with the effect of the N-long chain acyl-neutral amino acid polyglycerin ester or the nonionic surfactant composition of the present invention. The optional surfactants include, for example, anionic surfactants such as N-long chain acylamino acid salts, e.g., N-long chain acyl-acidic amino acid salts, N-long chain acyl-neutral amino acid salts, etc., N-long chain fatty acid acyl-N-methyltaurine salts, alkyl sulfates and their alkylene oxide adducts, fatty acid amide-ether sulfates, metal salts and weak base salts of fatty acids, sulfosuccinic acid-based surfactants, alkyl phosphates cream, hair liquid, hair-setting lotion, permanent-waving liquid, hair cream, hair lotion, hair mousse, shampoo, hair rinse, hair conditioner, body shampoo, solid detergent, liquid detergent, sweat-controlling agents, after-shaving cream, sunburn-protecting cream, sunburn-protecting oil, hair tonic, hair-growing agents, bathing agents, pharmaceutical compositions for external use, etc. The N-long chain acyl-neutral amino acid polyglycerin ester can be of course in the form of a nonionic surfactant composition of the present invention. The form of the cosmetic compositons and the percutaneous preparations is not specifically limited, and may be any type of emulsions, solutions, solubilizable mixtures, powdery dispersions, water-oil two-phase liquids, water-oil-powder three phase liquids, etc.

As the oily phase ingredients for the cosmetic compositions and the percutaneous preparations of the present invention are employable any ordinary ones within the range not interfering with the effect of the N-long chain acyl-neutral amino acid polyglycerin ester or the nonionic surfactant composition of the present invention. As such oily phase ingredients, there may be mentioned, for example, saturated or unsaturated fatty acids and higher alcohols to be derived therefrom, squalane, castor oil and their derivatives, bees wax, lanolins including liquid and pure lanolins, and their derivatives, cholesterol and its derivatives; animal and and their alkylene oxide adducts, alkyl ether-carboxylic acids, etc.; nonionic surfactants such as ether-type surfactants, e.g., glycerin ethers and their alkylene oxide adducts, etc., ester-type surfactants, e.g., glycerin esters and their alkylene oxide adducts, etc., ether-ester-type surfactants, e.g., sorbitan esters and their alkylene oxide adducts, etc., ester-type surfactants, e.g., polyoxyalkylene fatty acid esters, glycerin esters, fatty acid polyglycerin esters, N-long chain acyl-peptide polyglycerin esters, sorbitan esters, sucrose fatty acid esters, etc., alkylglucosides, hardened castor oil pyroglutamic acid diesters ad their ethylene oxide adducts, as well as nitrogen-containing nonionic surfactants, e.g., fatty acid alkanolamines, etc.; cationic surfactants such as aliphatic amines and their quaternary ammonium salts, e.g., alkylammonium chlorides, dialkylammonium chlorides, etc., aromatic quaternary ammonium salts, e.g., benzalkonium salts, etc., fatty acid acylarginine esters, etc.; as well as amphoteric surfactants such as betaine-type surfactants, e.g., carboxybetaines, etc., aminocarboxylic acid-based surfactants, imidazoline-based surfactants, etc.

The cosmetic compositions and the percutaneous preparations of the present invention may further contain, as an aqueous phase component, any of amino acids such as glycine, alanine, serine, threonine, arginine, glutamic acid, aspartic acid, leucine, valine, etc.; polyalcohols such as glycerin, ethylene glycol, 1,3-butylene glycol, propylene glycol, isoprene glycol, etc.; water-soluble polymers such as polyamino acids including polyglutamic acid and polyaspartic acid and their salts, polyethylene glycol, arabic gum, alginic acid salts, xanthane gum, hyaluronic acid, salts of hyaluronic acid, chitin, chitosan, water-soluble chitin, carboxyvinyl polymers, carboxymethyl cellulose, hydroxyethyl cellulose, hydroxypropyltrimethylammonium chloride, polydimethylmethylenepiperidium chloride, quaternary ammonium salts of polyvinylpyrrolidone derivatives, cationated proteins, collagen decomposates and their derivatives, acylated proteins, polyglycerins, amino acid polyglycerin esters, etc.; glycoalcohols such as mannitol, etc., and their alkylene oxide adducts; as well as lower alcohols such as ethanol, propanol, etc.

Any additives and pharmaceutical ingredients capable of being formulated in ordinary cosmetic compositions and percutaneous preparations can be incorporated into the cosmetic compositions and the percutaneous preparations of the present invention. For example, any of preservatives such as paraben derivatives, etc., as well as Perfumes, dyes, viscosity-controlling agents, pearly agents, antioxidants, microbicides, anti-inflammatory agents, analgesics, fungicides, keratin-softening and peeling agents, skin colorants, hormonic agents, UV absorbents, hair-growing agents, skin-whitening agents, sweat-controlling agents, sweat-deodorizing agents, vitamins, pH-controlling agents, pharmaceutical agents such as herbs, etc.

The amount of the N-long chain acyl-neutral amino acid polyglycerin ester or the nonionic surfactant composition comprising, as an active ingredient, at least one kind of such ester to be incorporated into the cosmetic compositions and the percutaneous preparations that may be prepared by suitably formulating the components noted above may vary, depending on the form of the products, but, in general, it may be from 0.01 to 100% by weight (the nonionic surfactant composition of the invention may be directly used as it is, for example, for makeup removal, without being combined with any other components), but preferably from 0.1 to 50% by weight, The invention is described in more detail hereinunder with reference to the following Examples, which, however, are not intended to restrict the scope of the present invention.

EXAMPLE 1

Production of mono(N-myristoyl-N-methyl-β-alanine) decaglycerin ester (MMMA-10)

313 g of N-myristoyl-N-methyl-β-alanine (manufactured by Kawaken Fine Chemical Co.) and 256 g of methanol were put into a 1000 ml flask, to which was added 2.85 g of p-toluenesulfonic acid as catalyst, and the mixture was heated for reaction under reflux for 5 hours. After its acid value was confirmed to be not larger than 10, the reaction mixture was neutralized with 1.2 g of an aqueous solution of sodium hydroxide (50%), and then the methanol was evaporated away under reduced pressure. The resulting residue was washed with water and dried to obtain N-myristoyl-N-methyl-β-alanine methyl ester. A 163 g portion of this N-myristoyl-N-methyl-β-alanine methyl ester and 379 g of decaglycerin (manufactured by Sakamoto Pharmaceutical Industry Co.), and then 1.1 g of sodium hydroxide were put into a 1000 ml flask, the atmosphere of which was then replaced with nitrogen. Then, the mixture was subjected to transesterification reaction by keeping it at 150° C. and not more than 60 mmHg for 6 hours to obtain 460 g of a pasty or oily product.

As a result of its analysis, the product was identified as a compound having an acid value of 0.02, a saponification value of 52.7 (theoretical: 53.2), and a hydroxyl value of 582 (theoretical: 585).

The IR absorption spectroscopy of this compound gave characteristic absorption bands at wave numbers of 3350 cm$^{-1}$ (hydroxyl group), 2900 cm$^{-1}$ (C—H), 1730 cm$^{-1}$ (ester), 1620 cm$^{-1}$ (amide), and 1150 cm$^{-1}$ (ether).

EXAMPLE 2

Production of penta(N-myristoyl-N-methyl-β-alanine) decaglycerin ester (PMMA-10)

N-myristoyl-N-methyl-β-alanine methyl ester was obtained in the same manner as in Example 1. A 409 g portion of this N-myristoyl-N-methyl-β-alanine methyl ester and 189 g of decaglycerin (manufactured by Sakamoto Pharmaceutical Industry Co.), and then 1.2 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 503 g of a pasty or oily product.

As a result of its analysis, the product was identified as a compound having an acid value of 0.09, a saponification value of 127.5 (theoretical: 125.5), and a hydroxyl value of 163 (theoretical: 175).

The IR absorption spectroscopy of this compound gave characteristic absorption bands at wave numbers of 3400 cm$^{-1}$ (hydroxyl group), 2900 cm$^{-1}$ (C—H), 1730 cm$^{-1}$ (ester), 1630 cm$^{-1}$ (amide), and 1120 cm$^{-1}$ (ether).

EXAMPLE 3

Production of tri(N-mixed fatty acid-acylalanine) decaglycerin ester (TCAA-10)

268 g of N-mixed fatty acid-acylalanine (composition of the acyl groups (by weight); capryl group: 11.3%, caproyl group: 9.4%, lauroyl group: 58.7%, myristoyl group: 18.5%, and palmitoyl group: 2.1%) and 256 g of methanol were put into a 1000 ml flask, to which was added 2.62 g of p-toluenesulfonic acid as catalyst, and the mixture was heated for reaction under reflux for 5 hours. After its acid value was confirmed to be not larger than 10, the reaction mixture was neutralized with 1.1 g of an aqueous solution of sodium hydroxide (50%), and then the methanol was distilled away under reduced pressure. The resulting residue was washed with water and dried to obtain N-mixed fatty acid-acylalanine methyl ester. A 255 g portion of this N-mixed fatty acid-acylalanine methyl ester and 227 g of decaglycerin (manufactured by Sakamoto Pharmaceutical Industry Co.), and then 1.0 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 411 g of a pasty or oily product.

As a result of its analysis, the product was identified as a compound having an acid value of 0.26, a saponification value of 114.2 (theoretical: 110.8), and a hydroxyl value of 327 (theoretical: 332).

EXAMPLE 4

Production of mono(N-myristoyl-N-methyl-β-alanine) hexaglycerin ester (MMMA-6)

N-myristoyl-N-methyl-β-alanine methyl ester was obtained in the same manner as in Example 1. A 164 g portion of this N-myristoyl-N-methyl-β-alanine methyl ester and 231 g of hexaglycerin (manufactured by Sakamoto Pharmaceutical Industry Co.), and then 0.79 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 321 g of a pasty or oily product.

As a result of its analysis, the product was identified as a compound having an acid value of 0.07, a saponification value of 73.6 (theoretical: 74.0), and a hydroxyl value of 501 (theoretical: 518).

The IR absorption spectroscopy of this compound gave characteristic absorption bands at wave numbers of 3350 cm$^{-1}$ (hydroxyl group), 2900 cm$^{-1}$ (C—H), 1730 cm$^{-1}$ (ester), 1630 cm$^{-1}$ (amide), and 1100 cm$^{-1}$ (ether).

EXAMPLE 5

Production of di(N-myristoyl-N-methyl-β-alanine) hexaglycerin ester (DMMA-6)

N-myristoyl-N-methyl-β-alanine methyl ester was obtained in the same manner as in Example 1. A 327 g portion of this N-myristoyl-N-methyl-β-alanine methyl ester and 231 g of hexaglycerin (manufactured by Sakamoto Pharmaceutical Industry Co.), and then 1.1 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 487 g of an oily product.

As a result of its analysis, the product was identified as a compound having an acid value of 0.01, a saponification value of 107.2 (theoretical: 106.5), and a hydroxyl value of 315 (theoretical: 319).

EXAMPLE 6

Production of tri(N-myristoyl-N-methyl-β-alanine) hexaglycerin ester (TMMA-6)

N-myristoyl-N-methyl-β-alanine methyl ester was obtained in the same manner as in Example 1. A 293 g portion of this N-myristoyl-N-methyl-β-alanine methyl ester and 138 g of hexaglycerin (manufactured by Sakamoto Pharmaceutical Industry Co.), and then 0.86 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 366 g of an oily product.

As a result of its analysis, the product was identified as a compound having an acid value of 0.11, a saponification value of 126.4 (theoretical: 124.7), and a hydroxyl value of 182 (theoretical: 207).

The IR absorption spectroscopy of this compound gave characteristic absorption bands at wave numbers of 3375 cm$^{-1}$ (hydroxyl group), 2900 cm$^{-1}$ (C—H), 1730 cm$^{-1}$ (ester), 1630 cm$^{-1}$ (amide), and 1120 cm$^{-1}$ (ether).

The electrospray ionization mass spectrometric analysis confirmed a value of 1350 (M+H)+.

EXAMPLE 7

Production of tri(N-coconut oil fatty acid-acylalanine) hexaglycerin ester (TCAA-6)

270 g of N-coconut oil fatty acid-acylalanine and 256 g of methanol were put into a 1000 ml flask, to which was added 2.63 g of p-toluenesulfonic acid as catalyst, and the mixture was heated for reaction under reflux for 5 hours. After its acid value was confirmed to be not larger than 10, the reaction mixture was neutralized with 1.1 g of an aqueous solution of sodium hydroxide (50%), and then the methanol was evaporated away under reduced pressure. The resulting residue was washed with water and dried to obtain N-coconut oil fatty acid-acylalanine methyl ester. A 256 g portion of this N-coconut oil fatty acid-acylalanine methyl ester and 139 g of hexaglycerin (manufactured by Sakamoto Pharmaceutical Industry Co.), and then 0.96 g of sodium hydroxide were put into a 1000 ml flask, the atmosphere of which was then replaced with nitrogen Then, transesterification reaction was carried out by keeping the mixture at 150° C. and not more than 60 mmHg for 6 hours to obtain 322 g of an oily product.

As a result of its analysis, the product was identified as a compound having an acid value of 0.18, a saponification value of 141.5 (theoretical: 137.6), and a hydroxyl value of 230 (theoretical: 229).

The IR absorption spectroscopy of this compound gave characteristic absorption bands at wave numbers of 3300 cm$^{-1}$ (hydroxyl group), 2900 cm$^{-1}$ (C—H), 1740 cm$^{-1}$ (ester), 1640 cm$^{-1}$ (amide), and 1120 cm$^{-1}$ (ether).

EXAMPLE 8

Production of tri(N-coconut oil fatty acid-acylglycine) hexaglycerin ester (TCGA-6)

256 g of N-coconut oil fatty acid-acylglycine and 256 g of methanol were put into a 1000 ml flask, to which was added 2.56 g of p-toluenesulfonic acid as catalyst, and the mixture was heated for reaction under reflux for 5 hours. After its acid value was confirmed to be not larger than 10, the reaction mixture was neutralized with 1.1 g of an aqueous solution of sodium hydroxide (50%), and then the methanol was evaporated away under reduced pressure. The resulting residue was washed with water and dried to obtain N-coconut oil fatty acid-acylglycine methyl ester. A 322 g portion of this N-coconut oil fatty acid-acylglycine methyl ester and 184 g of hexaglycerin (manufactured by Sakamoto Pharmaceutical Industry Co.), and then 1.0 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 454 g of a pasty product.

As a result of its analysis, the product was identified as a compound having an acid value of 0.81, a saponification value of 141.8 (theoretical: 142.5), and a hydroxyl value of 252 (theoretical: 237).

EXAMPLE 9

Production of tetra(N-coconut oil fatty acid-acylglycine) hexaglycerin ester (TTCGA-6)

N-coconut oil fatty acid-acylglycine methyl ester was obtained in the same manner as in Example 8. A 322 g portion of this N-coconut oil fatty acid-acylglycine methyl ester and 138 g of hexaglycerin (manufactured by Sakamoto Pharmaceutical Industry Co.), and then 0.76 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 388 g of a pasty product.

As a result of its analysis, the product was identified as a compound having an acid value of 0.67, a saponification value of 153.2 (theoretical: 158.0), and a hydroxyl value of 186 (theoretical: 158).

EXAMPLE 10

Production of tetra(N-myristoyl-N-methyl-β-alanine) decaglycerin ester (TTMMA-10)

N-myristoyl-N-methyl-β-alanine methyl ester was obtained in the same manner as in Example 1. A 326 g portion of this N-myristoyl-N-methyl-β-alanine methyl ester and 189 g of decaglycerin (manufactured by Sakamoto Pharmaceutical Industry Co.), and then 1.0 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 453 g of a pasty or oily product.

As a result of its analysis, the product was identified as a compound having an acid value of 0.13, a saponification value of 115.8 (theoretical: 115.6), and a hydroxyl value of 232 (theoretical: 231).

EXAMPLE 11

Production of di(N-myristoyl-N-methyl-β-alanine) tetraglycerin ester (DMMA-4)

N-myristoyl-N-methyl-β-alanine methyl ester was obtained in the same manner as in Example 1. A 196 g portion of this N-myristoyl-N-methyl-β-alanine methyl ester and 94 g of tetraglycerin (manufactured by Sakamoto Pharmaceutical Industry Co.), and then 0.7 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 228 g of a pasty or oily product.

As a result of its analysis, the product was identified as a compound having an acid value of 0.06, a saponification value of 122.2 (theoretical: 123.9), and a hydroxyl value of 256 (theoretical: 247).

The IR absorption spectroscopy of this compound gave characteristic absorption bands at wave numbers of 3400 cm$^{-1}$ (hydroxyl group), 2900 cm$^{-1}$ (C—H), 1745 cm$^{-1}$ (ester), 1640 cm$^{-1}$ (amide), and 1130 cm$^{-1}$ (ether).

EXAMPLE 12

Production of penta(N-coconut oil fatty acid-acylalanine) decaglycerin ester (PCAA-10)

N-coconut oil fatty acid-acylalanine methyl ester was obtained in the same manner as in Example 7. A 284 g portion of this N-coconut oil fatty acid-acylalanine methyl ester and 151 g of decaglycerin (manufactured by Sakamoto Pharmaceutical Industry Co.), and then 0.87 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 369 g of a pasty or oily product.

As a result of its analysis, the product was identified as a compound having an acid value of 0.12, a saponification value of 137.3 (theoretical: 138.5), and a hydroxyl value of 225 (theoretical: 193).

The IR absorption spectroscopy of this compound gave characteristic absorption bands at wave numbers of 3300 cm$^{-1}$ (hydroxyl group), 2925 cm$^{-1}$ (C—H), 1740 cm$^{-1}$ (ester), 1650 cm$^{-1}$ (amide), and 1120 cm$^{-1}$ (ether).

EXAMPLE 13

Production of tetra(N-coconut oil fatty acid-acylalanine) hexaglycerin ester (TTCAA-6)

N-coconut oil fatty acid-acylalanine methyl ester was obtained in the same manner as in Example 7. A 339 g portion of this N-coconut oil fatty acid-acylalanine methyl ester and 138 g of hexaglycerin (manufactured by Sakamoto Pharmaceutical Industry Co.), and then 0.95 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 418 g of an oily product.

As a result of its analysis, the product was identified as a compound having an acid value of 0.14, a saponification value of 154.1 (theoretical: 152.0), and a hydroxyl value of 175 (theoretical: 152).

EXAMPLE 14

Production of di(N-coconut oil fatty acid-acylalanine) tetraglycerin ester (DCAA-4)

N-coconut oil fatty acid-acylalanine methyl ester was obtained in the same manner as in Example 7. A 226 g portion of this N-coconut oil fatty acid-acylalanine methyl ester and 125 g of tetraglycerin (manufactured by Sakamoto Pharmaceutical Industry Co.), and then 0.95 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 209 g of an oily product.

As a result of its analysis, the product was identified as a compound having an acid value of 0.17, a saponification value of 138.0 (theoretical: 136.6), and a hydroxyl value of 290 (theoretical: 273).

The IR absorption spectroscopy of this compound gave characteristic absorption bands at wave numbers of 3300 cm$^{-1}$ (hydroxyl group), 2925 cm$^{-1}$ (C—H), 1745 cm$^{-1}$ (ester), 1650 cm$^{-1}$ (amide), and 1120 cm$^{-1}$ (ether).

EXAMPLE 15

Production of tri(N-coconut oil fatty acid-acylalanine) tetraglycerin ester (TCAA-4)

N-coconut oil fatty acid-acylalanine methyl ester was obtained in the same manner as in Example 7. A 255 g portion of this N-coconut oil fatty acid-acylalanine methyl ester and 94 g of tetraglycerin (manufactured by Sakamoto Pharmaceutical Industry Co.), and then 0.94 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 301 g of an oily product.

As a result of its analysis, the product was identified as a compound having an acid value of 0.17, a saponification value of 159.5 (theoretical: 156.6), and a hydroxyl value of 179 (theoretical: 156).

EXAMPLE 16

Production of tri(N-coconut oil fatty acid-acylglycine) tetraglycerin ester (TCGA-4)

N-coconut oil fatty acid-acylglycine methyl ester was obtained in the same manner as in Example 8. A 243 g portion of this N-coconut oil fatty acid-acylglycine methyl ester and 94 g of tetraglycerin (manufactured by Sakamoto Pharmaceutical Industry Co.), and then 0.84 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 298 g of a pasty product.

As a result of its analysis, the product was identified as a compound having an acid value of 0.33, a saponification value of 162.1 (theoretical: 163.0), and a hydroxyl value of 185 (theoretical: 163).

EXAMPLE 17

Production of di(N-coconut oil fatty acid-acylglycine) tetraglycerin ester (DCGA-4)

N-coconut oil fatty acid-acylglycine methyl ester was obtained in the same manner as in Example 8. A 270 g portion of this N-coconut oil fatty acid-acylglycine methyl ester and 157 g of tetraglycerin (manufactured by Sakamoto Pharmaceutical Industry Co.), and then 0.85 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 371 g of a pasty product.

As a result of its analysis, the product was identified as a compound having an acid value of 0.20, a saponification value of 139.2 (theoretical: 141.0), and a hydroxyl value of 301 (theoretical: 283).

The IR absorption spectroscopy of this compound gave characteristic absorption bands at wave numbers of 3300 cm$^{-1}$ (hydroxyl group), 2925 cm$^{-1}$ (C—H), 1740 cm$^{-1}$ (ester), 1640 cm$^{-1}$ (amide), and 1150 cm$^{-1}$ (ether).

EXAMPLE 18

Production of penta(N-coconut oil fatty acid-acylglycine) decaglycerin ester (PCGA-10)

N-coconut oil fatty acid-acylglycine methyl ester was obtained in the same manner as in Example 8. A 270 g portion of this N-coconut oil fatty acid-acylglycine methyl ester and 151 g of decaglycerin (manufactured by Sakamoto Pharmaceutical Industry Co.), and then 0.84 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 323 g of a pasty product.

As a result of its analysis, the product was identified as a compound having an acid value of 0.36, a saponification value of 143.4 (theoretical: 143.4), and a hydroxyl value of 226 (theoretical: 200).

EXAMPLE 19

Production of hexa(N-myristoyl-N-methyl-β-alanine) decaglycerin ester (HMMA-10)

N-myristoyl-N-methyl-β-alanine methyl ester was obtained in the same manner as in Example 1. A 393 g portion of this N-myristoyl-N-methyl-β-alanine methyl ester and 151 g of decaglycerin (manufactured by Sakamoto Pharmaceutical Industry Co.), and then 1.08 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 455 g of an oily product.

As a result of its analysis, the product was identified as a compound having an acid value of 0.07, a saponification value of 131.2 (theoretical: 132.9), and a hydroxyl value of 146 (theoretical: 132).

EXAMPLE 20

Production of tetra(N-myristoyl-N-methyl-β-alanine) hexaglycerin ester (TTMMA-6)

N-myristoyl-N-methyl-β-alanine methyl ester was obtained in the same manner as in Example 1. A 392 g portion of this N-myristoyl-N-methyl-β-alanine methyl ester and 138 g of hexaglycerin (manufactured by Sakamoto Pharmaceutical Industry Co.), and then 1.06 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 479 g of an oily product.

As a result of its analysis, the product was identified as a compound having an acid value of 0.09, a saponification value of 134.6 (theoretical: 136.4), and a hydroxyl value of 149 (theoretical: 136).

EXAMPLE 21

Production of tri(N-myristoyl-N-methyl-β-alanine) tetraglycerin ester (TMMA-4)

N-myristoyl-N-methyl-β-alanine methyl ester was obtained in the same manner as in Example 1. A 294 g portion of this N-myristoyl-N-methyl-β-alanine methyl ester and 94 g of tetraglycerin (manufactured by Sakamoto Pharmaceutical Industry Co.), and then 1.08 g of sodium hydroxide were put into a 1000 ml flask, the atmosphere of which was then replaced with nitrogen. Then, transesterification reaction was carried out by keeping the mixture at 150° C. and not more than 60 mmHg for 6 hours to obtain 340 g of an oily product.

As a result of its analysis, the product was identified as a compound having an acid value of 0.10, a saponification value of 138.3 (theoretical: 140.1), and a hydroxyl value of 142 (theoretical: 140).

The electrospray ionization mass spectrometric analysis confirmed a value of 1201 (M+H)+.

EXAMPLE 22

Production of mono(N-coconut oil fatty acid-acylsarcosine) decaglycerin ester (MCSA-10)

81 g of N-coconut oil fatty acid-acylsarcosine, 227 g of decaglycerin (manufactured by Sakamoto Pharmaceutical Industry Co.), and 1.54 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.55 g of an aqueous solution of sodium hydroxide (50%), and the water was removed therefrom at 95 to 105° C. and 60 mmHg to obtain 260 g of an oily product.

As a result of its analysis, the product was identified as a compound having an acid value of 1.55, a saponification value of 53.8 (theoretical: 55.4), and a hydroxyl value of 601 (theoretical: 610).

EXAMPLE 23

Production of mono(N-coconut oil fatty acid-acylsarcosine) tetraglycerin ester (MCSA-4)

135 g of N-coconut oil fatty acid-acylsarcosine, 157 g of tetraglycerin (manufactured by Sakamoto Pharmaceutical Industry Co.), and 1.46 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.43 g of an aqueous solution of sodium hydroxide (50%), and the water was removed therefrom at 95 to 105° C. and 60 mmHg to obtain 237 g of an oily product.

As a result of its analysis, the product was identified as a compound having an acid value of 1.05, a saponification value of 100.2 (theoretical: 98.9), and a hydroxyl value of 479 (theoretical: 494).

EXAMPLE 24

Production of tri(N-coconut oil fatty acid-acylsarcosine) decaglycerin ester (TCSA-10)

161 g of N-coconut oil fatty acid-acylsarcosine, 151 g of decaglycerin (manufactured by Sakamoto Pharmaceutical Industry Co.), and 1.56 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.61 g of an aqueous solution of sodium hydroxide (50%), and the water was removed therefrom at 95 to 105° C. and 60 mmHg to obtain 258 g of an oily product.

As a result of its analysis, the product was identified as a compound having an acid value of 0.60, a saponification value of 109.2 (theoretical: 110.9), and a hydroxyl value of 320 (theoretical: 332).

EXAMPLE 25

Production of mono(N-coconut oil fatty acid-acylalanine) hexaglycerin ester (MCAA-6)

135 g of N-coconut oil fatty acid-acylalanine, 231 g of hexaglycerin (manufactured by Sakamoto Pharmaceutical Industry Co.), and 1.83 g of sulfuric acid as catalyst were put into a 1000 ml flask. Dehydration condensation reaction was carried out by keeping the mixture in a nitrogen stream atmosphere at 150° C. for 8 hours. The reaction mixture was neutralized with 2.98 g of an aqueous solution of sodium hydroxide (50%), and the water was removed therefrom at 95 to 105° C. and 60 mmHg to obtain 311 g of an oily product.

As a result of its analysis, the product was identified as a compound having an acid value of 1.27, a saponification value of 77.2 (theoretical: 78.4), and a hydroxyl value of 533 (theoretical: 549).

The IR absorption spectroscopy of this compound gave characteristic absorption bands at wave numbers of 3300 $cm^{-1}$ (hydroxyl group), 2900 $cm^{-1}$ (C—H), 1730 $cm^{-1}$ (ester), 1640 $cm^{-1}$ (amide), and 1100 $cm^{-1}$ (ether).

EXAMPLE 26

Production of mono(N-lauroyl-N-methyl-β-alanine) tetraglycerin ester (MLMA-4)

142 g of N-lauroyl-N-methyl-β-alanine, 157 g of tetraglycerin (manufactured by Sakamoto Pharmaceutical Industry Co.) and 1.49 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.44 g of an aqueous solution of sodium hydroxide (50%), and the water was removed therefrom at 95 to 105° C. and 60 mmHg to obtain 235 g of an oily product.

As a result of its analysis, the product was identified as a compound having an acid value of 1.07, a saponification value of 97.2 (theoretical: 96.5), and a hydroxyl value of 479 (theoretical: 482).

EXAMPLE 27

Production of di(N-lauroyl-β-alanine) tetraglycerin ester (DLBA-4)

271 g of N-lauroyl-β-alanine, 157 g of tetraglycerin (manufactured by Sakamoto Pharmaceutical Industry Co.), and 1.46 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.39 g of an aqueous solution of sodium hydroxide (50%), and the water was removed therefrom at 95 to 105° C. and 60 mmHg to obtain 377 g of an oily product.

As a result of its analysis, the product was identified as a compound having an acid value of 0.97, a saponification value of 137.1 (theoretical: 136.6), and a hydroxyl value of 288 (theoretical: 273).

EXAMPLE 28

Production of mono(N-lauroyl-γ-aminobutyric acid) tetraglycerin ester (MLγA-4)

142 g of N-lauroyl-γ-aminobutyric acid, 157 g of tetraglycerin (manufactured by Sakamoto Pharmaceutical Industry Co.), and 1.49 g of sulfuric acid as catalyst were put into a 1000 ml flask. Dehydration condensation reaction was then carried out by keeping the mixture in a nitrogen stream atmosphere at 150° C. for 8 hours. The reaction mixture was neutralized with 2.45 g of an aqueous solution of sodium hydroxide (50%), and the water was removed therefrom at 95 to 105° C. and 60 mmHg to obtain 299 g of an oily product.

As a result of its analysis, the product was identified as a compound having an acid value of 1.04, a saponification value of 77.1 (theoretical: 76.9), and a hydroxyl value of 388 (theoretical: 384).

EXAMPLE 29

Production of mono(N-stearoylalanine) hexaglycerin ester (MSAA-6)

106 g of N-stearoylalanine, 138 g of hexaglycerin (manufactured by Sakamoto Pharmaceutical Industry Co.), and 1.22 g of sulfuric acid as catalyst were put into a 1000 ml flask. Dehydration condensation reaction was carried out by keeping the mixture in a nitrogen stream atmosphere at 150° C. for 8 hours. The reaction mixture was neutralized with 2.00 g of an aqueous solution of sodium hydroxide (50%), and the water was removed therefrom at 95 to 105° C. and 60 mmHg to obtain 194 g of an oily product.

As a result of its analysis, the product was identified as a compound having an acid value of 0.97, a saponification value of 72.7 (theoretical: 70.1), and a hydroxyl value of 477 (theoretical: 491).

EXAMPLE 30

Production of di(N-coconut oil fatty acid-acylalanine) tetraglycerin ester (DCAA-4)

123 g of N-coconut oil fatty acid-acylalanine, 66 g of tetraglycerin (manufactured by Sakamoto Pharmaceutical Industry Co.), and 1.83 g of sulfuric acid as catalyst were put into a 1000 ml flask. Dehydration condensation reaction was carried out by keeping the mixture in a nitrogen stream atmosphere at 150° C. for 8 hours. The reaction mixture was neutralized with 2.98 g of an aqueous solution of sodium hydroxide (50%), and the water was removed therefrom at 95 to 105° C. and 60 mmHg to obtain 140 g of an oily product.

As a result of its analysis, the product was identified as a compound having an acid value of 16.7.

The 140 g oily product was added with 750 g of n-hexane and heated up to about 50° C. The mixture was then allowed to stand whereby separate layers were formed. The hexane layer was removed. The hexane remaining in the DCAA-4 layer was removed at 60 mmHg and 95 to 150° C. to obtain 103 g of an oily product.

As a result of its analysis, the product was identified as a compound having an acid value of 6.0.

REFERENCE EXAMPLE 1

Production of mono(N-myristoyl-N-methyl-β-alanine) diglycerin ester (MMMA-2)

N-myristoyl-N-methyl-β-alanine methyl ester was obtained in the same manner as in Example 1. A 327 g portion of this N-myristoyl-N-methyl-β-alanine methyl ester and 166 g of diglycerin (manufactured by Sakamoto Pharmaceutical Industry Co.), and then 1.00 g of sodium hydroxide were put into a 1000 ml flask, and the atmosphere of which was then replaced with nitrogen. Then, transesterification reaction was then carried out by keeping the mixture at 150° C. and not more than 60 mmHg for 6 hours to obtain 447 g of an oily product.

As a result of its analysis, the product was identified as a compound having an acid value of 0.01, a saponification value of 119.1 (theoretical: 121.5), and a hydroxyl value of 383 (theoretical: 364).

REFERENCE EXAMPLE 2

Production of mono(N-lauroylalanine) diglycerin ester (MLAA-2)

162 g of N-lauroylalanine, 99 g of diglycerin (manufactured by Sakamoto Pharmaceutical Industry Co.), and 1.30 g of sulfuric acid as catalyst were put into a 1000 ml flask. Dehydration condensation reaction was carried out by keeping the mixture in a nitrogen stream atmosphere at 150° C. for 8 hours. The reaction mixture was neutralized with 2.14 g of an aqueous solution of sodium hydroxide (50%), and the water was removed therefrom at 95 to 105° C. and 60 mmHg to obtain 221 g of an oily product.

As a result of its analysis, the product was identified as a compound having an acid value of 0.82, a saponification value of 132.2 (theoretical: 134.1), and a hydroxyl value of 533 (theoretical: 536).

The following formulation examples are to concretely demonstrate the effect of the N-long chain acyl-neutral amino acid polyglycerin esters of the present invention and the nonionic surfactant compositions comprising, as an active ingredient, at least one kind of such polyglycerin esters.

EXAMPLES 31 TO 46, AND COMPARATIVE EXAMPLES 1 AND 2

Milky Lotion

Using the N-long chain acyl-neutral amino acid polyglycerin esters of the present invention and the nonionic surfactant compositions comprising, as an active ingredient, at least one kind of such polyglycerin esters, as produced in the previous Examples and Reference Examples, milky lotion samples were prepared in accordance with the formulation shown in Table 1(a). Five panelists sensorially tested these samples, and evaluated them on the basis of the criteria shown in Table 1(b). From the points that each sample had gained, the samples were evaluated according to the method shown in Table 1(c).

The test results are shown in Table 2.

TABLE 1

(a) Formulation of Milky Lotion (wt. %):

| | |
|---|---|
| Nonionic Surfactant in Examples or Reference Examples | 4.0 |
| Octyl-dodecanol | 4.0 |
| Liquid Paraffin | 20.0 |
| Pure Water | 72.0 |

(b) Criteria for Evaluation:

2: Very good
    1: Good
    0: Average (Comparative Example 1)
    −1: Bad
    −2: very bad (c) Method for Evaluation:

The points that each sample had gained in the panelists' sensory test were averaged. The samples having gained an average point of from 1.0 to 2.0 were evaluated excellent (AA); those having gained an average point of from 0.5 to 1.0 were evaluated good (A); and those having gained an average point of from −0.5 to 0.5 were evaluated average (B). For the criteria for evaluation, the sample of Comparative Example 1 was the standard with point 0.

TABLE 2

Sensorial Test results of Milky Lotion Samples

| | | When applied to the skin | | | | After applied to the skin | |
|---|---|---|---|---|---|---|---|
| Example No. | Non-Ionic Surfactant | Spreadability | Smoothness | Compatibility | Refreshing Feel | Non-stickiness | Refreshing Feel |
| Example 31 | Compound of Ex. 2 (PMMA-10) | AA | AA | AA | A | A | A |
| Example 32 | Compound of Ex. 6 (TMMA-6) | AA | AA | A | AA | AA | A |
| Example 33 | Compound of Ex. 7 (TCAA-6) | AA | AA | AA | AA | A | B |
| Example 34 | Compound of Ex. 8 (TCGA-6) | AA | AA | AA | B | A | B |
| Example 35 | Compound of Ex. 9 (TTCGA-6) | AA | AA | AA | A | A | AA |
| Example 36 | Compound of Ex. 10 (TTMMA-10) | AA | AA | B | A | A | A |
| Example 37 | Compound of Ex. 11 (DMMA-4) | AA | AA | AA | A | A | A |
| Example 38 | Compound of Ex. 12 (PCAA-10) | AA | AA | AA | AA | AA | B |
| Example 39 | Compound of Ex. 13 (TTCAA-6) | AA | AA | AA | A | A | A |
| Example 40 | Compound of Ex. 14 (DCAA-4) | AA | AA | A | A | A | A |
| Example 41 | Compound of Ex. 15 (TCAA-4) | AA | AA | AA | AA | AA | AA |
| Example 42 | Compound of Ex. 16 (TCGA-4) | AA | AA | AA | B | AA | AA |
| Example 43 | Compound of Ex. 17 (DCGA-4) | AA | AA | AA | A | AA | A |
| Example 44 | Compound of Ex. 18 (PCGA-10) | A | AA | A | A | B | A |
| Example 45 | Compound of Ex. 19 (HMMA-10) | A | A | A | A | A | B |
| Example 46 | Compound of Ex. 20 (TTMMA-6) | AA | AA | AA | A | B | A |
| Comparative Example 1 | Compound of Ref. Ex. 1 (MMMA-2) | B | B | B | B | B | B |
| Comparative Example 2 | Compound of Ref. Ex. 2 (MLAA-2) | B | B | B | B | B | B |

EXAMPLES 47 AND 48, AND COMPARATIVE EXAMPLES 3 TO 8

Milky Lotion

Milky lotions were prepared in accordance with the formulations shown in Table 3 below, using the nonionic surfactant compounds of Examples 14 and 25 as well as the comparative nonionic surfactant fatty acid polyglycerin esters as control. The milky lotions were prepared by heating to 70° C. the ingredients under Components A and B separately, followed by adding gradually the ingredients under Component B to those under Component A. The resulting mixture was emulsified in a homomixer.

The milky lotions were evaluated about their stability in the emulsified state in the following manner. I.e., each lotion immediately after prepared was allowed to stand in a constant temperature room kept at 40° C. for one month. Then, the lotions were observed on their state. The evaluation criteria for the lotion stability is: A, if the emulsified state continued for one month at 40° C., whereas B, if the emulsified state had been broken down into two sepatate phases by the end of that one month. The results are shown also in Table 3 below.

ponent 3 were separately dissolved, and the resulting solution of the ingredients under Component 3 was added to and emulsified with those under Component 1. To the resulting emulsion were added the ingredients under Component 2 and the mixture was further emulsified in a homomixer to obtain a product of emollient lotion. In its sensorial test, the emollient lotion was well spreadable and smooth on the skin, while having good compatibility with the skin.

TABLE 3

|  | Examples | | Comparative Examples | | | | | |
| --- | --- | --- | --- | --- | --- | --- | --- | --- |
|  | 47 | 48 | 3 | 4 | 5 | 6 | 7 | 8 |
| (Component A) | | | | | | | | |
| Liquid paraffin | 23 | 23 | 23 | 23 | 23 | 23 | 23 | 23 |
| Cetanol | 1 | 1 | 1 | 1 | 1 | 1 | 1 | 1 |
| Glyceryl stearate | 2 | 2 | 2 | 2 | 2 | 2 | 2 | 2 |
| Compound of Ex. 14(DCAA-4) | 4 | | | | | | | |
| Compound of Ex. 25(MCAA-6) | | 4 | | | | | | |
| Tetraglyceryl laurate | | | 4 | | | | | 0.8 |
| Hexaglyceryl laurate | | | | 4 | | | | |
| Decaglyceryl laurate | | | | | 4 | | | 1.2 |
| Pentaglyceryl distearate | | | | | | 4 | | 2 |
| Pentaglyceryl diisostearate | | | | | | | 4 | |
| (Component B) | | | | | | | | |
| PEG400 | 3.1 | 3.1 | 3.1 | 3.1 | 3.1 | 3.1 | 3.1 | 3.1 |
| 1,3-Butylene glycol | 1.5 | 1.5 | 1.5 | 1.5 | 1.5 | 1.5 | 1.5 | 1.5 |
| Methylparaben | 0.2 | 0.2 | 0.2 | 0.2 | 0.2 | 0.2 | 0.2 | 0.2 |
| Pure water | Balance | Balance | Balance | Balance | Balance | Balance | Balance | Balance |
| Emulsion stability | A | A | B | B | B | B | B | B |

EXAMPLE 49

Lotion

A lotion having the composition shown in Table 4 below was formulated in an ordinary manner. I.e., the ingredients under Component 1 and those under Component 2 were separately dissolved, and the resulting solution of the ingredients under Component 2 was added to and mixed with that of the ingredients under Component 1. In its sensorial test, the lotion thus formulated was well spreadable on the skin, while having good compatibility with the skin and a good refreshing feel.

TABLE 4

| (Component 1) | |
| --- | --- |
| Propylene glycol | 6.0 |
| Glycerin | 3.0 |
| Sodium PCA(*) | 1.0 |
| Sodium polyaspartate solution (30%) | 0.5 |
| Pure Water | balance |
| (Component 2) | |
| Oleyl alcohol | 0.5 |
| TTCGA-6 (Example 9) | 1.0 |
| POE(20) sorbitan monolaurate | 0.5 |
| POE(15) lauryl alcohol ether | 0.5 |
| Ethanol | 10.0 |
| Perfume | ad lib. |
| Preservative | ad lib. |
| Total | 100% |

(*)PCA : pyrrolidonecarboxylic acid.

EXAMPLE 50

Emollient Lotion

An emollient lotion having the composition shown in Table 5 below was formulated in the following manner. I.e., the ingredients under Component 1 and those under Com-

TABLE 5

| (Component 1) | |
| --- | --- |
| Cetyl alcohol | 2.0 |
| Bees wax | 0.5 |
| Vaseline | 2.0 |
| Squalane | 6.0 |
| Dimethylpolysiloxane | 2.0 |
| TCAA-10 (Example 3) | 1.0 |
| POE(10) monooleate | 1.0 |
| (Component 2) | |
| Ethanol | 5.0 |
| Quince seed extract | 20.0 |
| (aqueous 20% solution) | |
| (Component 3) | |
| Perfume | ad lib. |
| Preservative | ad lib. |
| Pure water | balance |
| Total | 100% |

EXAMPLE 51

W/O Milky Lotion

A W/O milky lotion having the composition shown in Table 6 below was formulated in an ordinary manner. In its sensorial test, the W/O milky lotion was well spreadable on the skin, while having good compatibility with the skin, and it was not sticky.

TABLE 6

| (Oily Phase) | |
|---|---|
| Di(cholesteryl, behenyl, octyl, dodecyl) lauroylglutamate | 7.0 |
| Squalane | 5.0 |
| Triglyceryl diisostearate | 0.5 |
| Glyceryl trioctanoate | 5.0 |
| PCGA-10 (Example 18) | 5.0 |
| Polydimethylsiloxane | 3.0 |
| POE dimethylsiloxane (HLB = 7) | 3.0 |
| Decamethylcyclopentasiloxane | 3.0 |
| (Aqueous Phase) | |
| Sodium chloride | 0.5 |
| Preservative | 0.2 |
| Deacetylated chitin | 0.03 |
| Glycerin | 5.0 |
| Perfume | ad lib. |
| Pure Water | balance |
| Total | 100% |

EXAMPLE 52

O/W Cream

An O/W cream having the composition shown in Table 7 below was formulated in the following manner. I.e., the oily phase ingredients were heated to 80° C., and the aqueous phase ingredients, to 50° C. While the oily phase was being stirred, the aqueous phase was gradually added thereto and emulsified. In its sensorial test, the O/W cream thus formulated was well spreadable on the skin, while having good compatibility with the skin, and it was not sticky.

TABLE 7

| (Oily Phase) | |
|---|---|
| Squalane | 8.0 |
| Liquid paraffin | 10.0 |
| Cetyl octanoate | 13.0 |
| PMMA-10 (Example 2) | 5.0 |
| Hardened oil | 5.0 |
| Behenyl alcohol | 1.0 |
| Stearic acid | 2.0 |
| Dimethylsiloxane | 0.3 |
| POE(20) sorbitan monooleate | 4.0 |
| (Aqueous Phase) | |
| Preservative | 0.2 |
| Sodium N-stearoyl-L-glutamate | 0.4 |
| Xanthane gum | 0.05 |
| 1,3-Butylene glycol | 4.0 |
| Glycine | 1.0 |
| Glycine betaine | 1.5 |
| N-coconut oil fatty acid-acyl-L-arginine ethyl ester pyrrolidonecarboxylate | 0.5 |
| Perfume | ad lib. |
| Pure water | balance |
| Total | 100% |

EXAMPLE 53

Milky Lotion

A milky lotion having the composition shown in Table 8 below was formulated in the following manner. I.e., the ingredients under Components 1, 2 and 3 were separately heated to 60° C. While the ingredients under Component 1 were being stirred, the ingredients under Component 2 and 3 were gradually added thereto in that order, and then cooled to 30° C. In its sensorial test, the milky lotion thus formulated was well spreadable on the skin, while having good compatibility with the skin.

TABLE 8

| (Component 1) | |
|---|---|
| 1,3-Butylene glycol | 1.2 |
| DMMA-4 (Example 11) | 4.0 |
| TTMMA-10 (Example 10) | 2.0 |
| (Component 2) | |
| Liquid paraffin | 20.0 |
| (Component 3) | |
| Perfume | ad lib. |
| Preservative | ad lib. |
| Pure water | balance |
| Total | 100% |

EXAMPLE 54

Emollient Cream

An emollient cream having the composition shown in Table 9 below was formulated in the following manner. I.e., the ingredients under Components 2 and 3 were separately heated to 50° C. The ingredients under Component 2 were gradually added to the ingredients under Component 3 to form a mixture. This mixture was added to and uniformly dispersed in a hot melt of the ingredients under Component 1 heated to 70° C. The ingredients under Component 4 were heated to 70° C., and added to the dispersion with fully stirring, and then emulsified in a homomixer to obtain a product of emollient cream. In its sensorial test, the emollient cream was well spreadable and smooth on the skin, while having good compatibility with the skin.

TABLE 9

| (Component 1) | |
|---|---|
| Liquid paraffin | 25.0 |
| Macadamia nut oil | 5.0 |
| Microcrystalline wax | 2.0 |
| Vaseline | 5.0 |
| (Component 2) | |
| DCAA-4 (Example 14) | 5.0 |
| TCAA-6 (Example 7) | 1.0 |
| Tocopherol acetate | 0.2 |
| (Component 3) | |
| Sodium glutamate | 1.6 |
| Serine | 0.4 |
| Pure water | 13.0 |
| (Component 4) | |
| Propylene glycol | 3.0 |
| Preservative | ad lib. |
| Perfume | ad lib. |
| Pure water | balance |
| Total | 100% |

EXAMPLE 55

UV-Cut Essence

A UV-cut essence having the composition shown in Table 10 below was formulated in the following manner. I.e., the moisturizer and triethanolamine were dissolved in pure water by heating to 70° C. The oily components were melted by heating to 70° C., to which were added the surfactant, the UV absorbent, the preservative and the perfume in that order, and uniformly dissolved in a homomixer at 70° C. In its sensorial test, the UV-cut essence thus formulated had a good refreshing feel with no stickiness.

TABLE 10

| (Component 1) | |
|---|---|
| Stearic acid | 3.0 |
| Cetanol | 1.0 |
| Lanolin derivative | 3.0 |
| Liquid paraffin | 5.0 |
| 2-Ethylhexyl stearate | 3.0 |
| (Component 2) | |
| 1,3-Butylene glycol | 6.0 |
| (Component 3) | |
| POE(10) cetyl alcohol ether | 2.0 |
| MLMA-4 (Example 26) | 2.0 |
| DLBA-4 (Example 27) | 1.0 |
| Glyceryl cetostearate | 1.0 |
| Triethanolamine | 1.0 |
| (Component 4) | |
| 2-Hydroxy-4-methoxybenzophenone | 4.0 |
| Dibenzoylmethane derivative | 4.0 |
| 2-Ethylhexyl dimethoxybenzylidene-dioxoimidazolidine-propionate | 2.0 |
| (Component 5) | |
| Perfume | ad lib. |
| Preservative | ad lib. |
| Pure water | balance |
| Total | 100% |

EXAMPLE 56

Suntan Oil

A suntan oil having the composition shown in Table 11 below was formulated in an ordinary manner. In its sensorial test, the suntan oil had a smooth feel with no stickiness.

TABLE 11

| Octyl paramethoxycinnamate | 2 |
|---|---|
| Squalane | 44 |
| Cetyl octanoate | 26 |
| Dihydroxyacetone | 4 |
| TCAA-10 (Example 3) | 24 |
| BHT(*) | ad lib. |
| Perfume | ad lib. |
| Total | 100% |

(*)BHT : dibutylhydroxytoluene.

EXAMPLE 57

W/O Foundation Cream

A W/O foundation cream having the composition shown in Table 12 below was formulated in the following manner. I.e., the ingredients under Component 3 were stirred, and the ingredients under Component 1 having been well ground were added thereto and processed in a homomixer. The ingredients under Component 2 were dissolved, and added to the mixture prepared previously, and then processed in a homomixer to obtain a product of W/O foundation cream. In its sensorial test, the W/O foundation cream was well spreadable on the skin and had a good smooth feel.

TABLE 12

| (Component 1) | |
|---|---|
| Talc | 7.0 |
| Titanium dioxide | 12.0 |
| Silicic anhydride | 2.0 |
| Nylon powder | 4.0 |
| Color pigment | 2.0 |
| (Component 2) | |
| Di(cholesteryl, behenyl, octyl, dodecyl) Lauroylglutamate | 2.0 |
| Di(phytosteryl, octyldodecyl) lauroylglutamate | 0.5 |
| MCSA-10 (Example 22) | 2.0 |
| Octamethylcyclotetrasiloxane | 10.0 |
| Polyoxyethylene-modified dimethylsiloxane | 1.5 |
| (Component 3) | |
| Preservative | ad lib. |
| Ethanol | 7.0 |
| 1,3-Butylene glycol | 1.0 |
| Sodium hyaluronate (aqueous 1% solution) | 1.0 |
| N-coconut oil fatty acid-acyl-L-arginine ethyl ester DL-pyrrolidonecarboxylate | 0.5 |
| Pure water | balance |
| Total | 100% |

EXAMPLE 58

Powdery Foundation

A powdery foundation having the composition shown in Table 13 below was formulated in the following manner. I.e., the ingredients under Component 1 (pigment components) were mixed and ground in a grinder. Next, the resulting mass was transferred into a high-performance blender, and a mixture of the ingredients under Components 2 and 3 having been previously prepared was added thereto and uniformly mixed. The resulting mixture was sieved for dressing to have a uniform grain size, and then shaped under pressure to obtain a product of powdery foundation. In its sensorial test, the powdery foundation had good compatibility with the skin and was well spreadable on the skin.

TABLE 13

| (Component 1) | |
|---|---|
| Talc | 20.0 |
| Mica | 35.0 |
| Kaolin | 5.0 |
| Titanium dioxide | 6.0 |
| Zinc stearate | 1.0 |
| Red iron oxide | 1.0 |
| Yellow iron oxide | 3.0 |
| Black iron oxide | 0.2 |
| Nylon powder | 10.0 |
| Lauroyllysine | 4.0 |
| (Component 2) | |
| Glyceryl pyroglutamate oleate | 0.5 |
| TMMA-6 (Example 6) | 2.0 |
| Lanolin | 1.0 |
| Squalane | 6.0 |
| Octyldodecyl Myristate | 2.0 |
| (Component 3) | |
| Preservative | ad lib. |
| Antioxidant | ad lib. |
| Perfume | ad lib. |
| Total | 100% |

EXAMPLE 59

All-Season Foundation

An all-season foundation having the composition shown in Table 14 below was formulated in the following manner. I.e., the ingredients under Component 1 were mixed and ground in a grinder. Next, the resulting mass was transferred into a high-performance blender, and a mixture of the ingredients under Components 2 and 3 having been previously prepared was added thereto and uniformly mixed. The resulting mixture was sieved for dressing to have a uniform grain size, and then shaped under pressure to obtain a product of all-season foundation. In its sensorial test, the all-season foundation had good compatibility with the skin and was well spreadable on the skin.

TABLE 14

| (Component 1) | |
|---|---|
| Silicone-processed talc | 19.0 |
| Silicone-processed mica | 38.0 |
| Lauroyllysine | 2.0 |
| Silicone-processed fine grains of titanium dioxide | 20.0 |
| Zinc stearate | 0.1 |
| Silicone-processed red iron oxide | 1.0 |
| Silicone-processed yellow iron oxide | 3.0 |
| Silicone-processed black iron oxide | 0.2 |
| Nylon powder | 2.0 |
| (Component 2) | |
| Squalane | 4.0 |
| Solid paraffin | 0.7 |
| TCGA-6 (Example 8) | 2.0 |
| Dimethylpolysiloxane | 4.0 |
| Glyceryl triisooctanoate | 2.0 |
| Octyl methoxycinnamate | 1.0 |
| (Component 3) | |
| Preservative | ad lib. |
| Antioxidant | ad lib. |
| Perfume | ad lib. |
| Total | 100% |

EXAMPLE 60

Cheek Rouge

A cheek rouge having the composition shown in Table 15 below was formulated in the following manner. I.e, titanium dioxide, kaolin, iron oxide (red) and Red #202 were added to a part of liquid paraffin, and dispersed therein with the use of a roller. The other ingredients were previously mixed and melted by heating. These were all mixed to form a uniform dispersion. The dispersion was cooled with stirring to obtain a product of cheek rouge. In its sensorial test, the cheek rouge had good compatibility with the skin with no stickiness, and was well spreadable on the skin.

TABLE 15

| Titanium dioxide | 4.2 |
|---|---|
| Kaolin | 18.0 |
| Lauroyllysine | 2.0 |
| Iron oxide (red) | 0.3 |
| Red #202 | 0.5 |
| Ceresine | 12.0 |
| Di(cholesteryl, octyldodecyl) lauroylglutamate | 3.0 |
| Vaseline | 20.0 |
| Liquid paraffin | 20.0 |

TABLE 15-continued

| HMMA-10 (Example 19) | 5.0 |
|---|---|
| Isopropyl myristate | 15.0 |
| Antioxidant | ad lib. |
| Perfume | ad lib. |
| Total | 100% |

EXAMPLE 61

Emulsion-Based Lip Stick

An emulsion-based lip stick having the composition shown in Table 16 below was formulated in the following manner. I.e., out of the ingredients under Component 1, titanium oxide, Red #201 and Red #202 were added to a part of castor oil, and dispersed therein with the use of a roller. Red #223 was dissolved in castor oil. The other ingredients under Component 1 were melted by heating, and uniformly dispersed along with the pigment and dye in a homomixer. The ingredients under Component 2 were dissolved by heating, and emulsified and dispersed in the mixture prepared previously, also in a homomixer. The resulting emulsion was cast into a mold and rapidly cooled to form lip sticks. In its sensorial test, the emulsion-based lip stick had good compatibility with the lips with no stickiness, and was well spreadable on the lips.

TABLE 15

| (Component 1) | |
|---|---|
| Titanium dioxide | 3.5 |
| Lauroyllysine | 1.0 |
| Red #201 | 0.5 |
| Red #202 | 2.0 |
| Red #223 | 0.05 |
| Ceresine | 4.0 |
| Candellila wax | 8.0 |
| Carnauba wax | 2.0 |
| Castor oil | 30.0 |
| MMMA-10 (Example 1) | 19.95 |
| TCGA-4 (Example 16) | 20.0 |
| POE(25)-POP(20) 2-tetradecyl ether | 1.0 |
| Preservative | ad lib. |
| Antioxidant | ad lib. |
| Perfume | ad lib. |
| (Component 2) | |
| Sodium polyaspartate solution (30%) | 1.0 |
| Pure water | 4.0 |
| Glycerin | 2.0 |
| Propylene glycol | 1.0 |
| Total | 100.0% |

EXAMPLE 62

Lip Stick

A lip stick having the composition shown in Table 17 below was formulated in the following manner. I.e, the ingredients under Component 2 were dissolved by heating, to which were added the ingredients under Component 1 and kneaded in a roll mill to form a uniform dispersion. After having been defoamed, this dispersion was cast into a mold and rapidly cooled to form lip sticks. In its sensorial test, the lip stick had good compatibility with the lips with no stickiness, and was well spreadable on the lips.

TABLE 17

| (Component 1) | |
|---|---|
| Titanium dioxide | 1.0 |
| Red #201 | 1.0 |
| Red #202 | 2.0 |
| Yellow #4 aluminium lake | 1.0 |
| Red #223 | 0.1 |
| (Component 2) | |
| Di(cholesteryl, octyldodecyl) lauroylglutamate | 6.0 |
| Candellila wax | 7.0 |
| Bees wax | 5.0 |
| Ozocerite | 4.0 |
| Carnauba wax | 2.0 |
| Castor oil | 49.9 |
| PCGA-10 (Example 18) | 5.0 |
| Octyldodecanol | 10.0 |
| Liquid lanolin | 5.0 |
| Preservative | ad lib. |
| Antioxidant | ad lib. |
| Perfume | ad lib. |
| Total | 100% |

EXAMPLE 63

Eyebrow Pencil

An eyebrow pencil having the composition shown in Table 18 below was formulated in the following manner. I.e., the powdery ingredients under Component 1 were well blended in a blender, and mixed with the other ingredients having been heat-melted. The mixture was ground and dispersed in a grinder, and the resulting dispersion was shaped under pressure to form a product of eyebrow stick. In its sensorial test, the eyebrow pencil produced had good compatibility with the skin with no stickiness, and was very good.

TABLE 18

| (Component 1) | |
|---|---|
| Titanium dioxide | 20.0 |
| Iron oxide (red) | 20.0 |
| Iron oxide (yellow) | 20.0 |
| Iron oxide (black) | 15.0 |
| Talc | 10.0 |
| Lanolin wax | 10.0 |
| MCSA-4 (Example 23) | 1.0 |
| Liquid paraffin | 3.0 |
| Glyceryl monostearate | 1.0 |
| Preservative | ad lib. |
| Antioxidant | ad lib. |
| Perfume | ad lib. |
| Total | 100% |

EXAMPLE 64

O/W Foundation Cream

An O/W foundation cream having the composition shown in Table 19 below was formulated in the following manner. I.e., out of the ingredients under Component 2, bentonite was dispersed in propylene glycol, and the resulting dispersion was added to pure water and processed at 70° C. in a homomixer. The remaining ingredients under Component 2 were added to the thus-processed dispersion and fully stirred. Next, the ingredients under Component 1 were mixed and ground, and added to the previous mixture with stirring, and thereafter processed in a homomixer at 70° C. Next, the ingredients under Component 3 having been heated to 70 to 80° C. were gradually added thereto, and further processed in the homomixer at 70° C. The resulting mass was cooled to room temperature to obtain a product of O/W foundation cream. In its sensorial test, the O/W foundation cream was well spreadable on the skin and had a good smooth feel.

TABLE 19

| (Component 1) | |
|---|---|
| Talc | 3.0 |
| Titanium dioxide | 5.0 |
| Red iron oxide | 0.5 |
| Yellow iron oxide | 1.4 |
| Black iron oxide | 0.1 |
| (Component 2) | |
| Bentonite | 0.5 |
| Polyoxyethylene sorbitan monostearate | 0.9 |
| MSAA-6 (Example 29) | 2.0 |
| Triethanolamine | 1.0 |
| Propylene glycol | 10.0 |
| Pure water | 54.4 |
| (Component 3) | |
| Stearic acid | 2.2 |
| Isohexadecyl alcohol | 7.0 |
| Glyceryl monostearate | 2.0 |
| Liquid lanolin | 2.0 |
| Liquid paraffin | 8.0 |
| Preservative | ad lib. |
| Total | 100% |

EXAMPLE 65

Conditioning Shampoo

A conditioning shampoo having the composition shown in Table 20 below was formulated in the following manner. I.e., cationated cellulose was added to pure water and stirred while being heated up to 70° C. The other ingredients were added thereto and dissolved with stirring. The resulting mass was cooled to obtain a product of conditioning shampoo. In its sensorial test, the conditioning shampoo had a good refreshing feel with no stickiness.

TABLE 20

| Lauryl POE(3) sulfate triethanolamine salt (30%) | 10.0 |
|---|---|
| Lauryl POE(3) sulfate sodium salt (30%) | 10.0 |
| Coconut oil fatty acid-acylalanine triethanolamine salt solution (30%) | 10.0 |
| Lauryl sulfate sodium salt (30%) | 5.0 |
| Lauryldiethanolamide | 3.0 |
| Betaine lauryldimethylaminoacetate | 7.0 |
| Cationated cellulose | 0.2 |
| PCAA-10 (Example 12) | 2.0 |
| Perfume | ad lib. |
| Preservative | ad lib. |
| pH-controlling agent | ad lib. |
| Pure water | balance |
| Total | 100% |

EXAMPLE 66

Rinse-In Shampoo

A rinse-in shampoo having the composition shown in Table 21 below was formulated in the following manner. I.e., stearyltrimethylammonium chloride and the amphoteric surfactant were dissolved in pure water by heating and kept at 70° C., and the remaining ingredients were added thereto and dissolved. The resulting mass was cooled to obtain a product of rinse-in shampoo. In its sensorial test, the rinse-in shampoo had a good refreshing feel with no stickiness.

TABLE 21

| | |
|---|---|
| Imidazolium-betaine amphoteric surfactant | 10.0 |
| Coconut oil fatty acid-acylglutamic acid triethanolamine salt solution (30%) | 6.0 |
| Coconut oil fatty acid-acyl-L-arginine ethyl ester DL-pyrrolidonecarboxylate | 1.0 |
| Coconut oil fatty acid diethanolamide | 4.0 |
| TMMA-4 (Example 21) | 2.0 |
| Stearyltrimethylammonium chloride | 2.0 |
| N-lauroyl-N-methyl-β-alanine sodium salt (30%) | 1.0 |
| Dimethylpolysiloxane | 1.0 |
| POE(2) stearylamine | 1.0 |
| Perfume | ad lib. |
| Dye | ad lib. |
| pH-controlling agent | ad lib. |
| Pure water | balance |
| Total | 100% |

EXAMPLE 67

Hair Treatment Cream

A hair treatment cream having the composition shown in Table 22 below was formulated in the following manner. I.e., the ingredients under Components 1 and 2 were separately heated to 80° C., and the ingredients under Component 1 were gradually added to the ingredients under Component 2 being stirred. The resulting mass was cooled to obtain a product of hair treatment cream. In its sensorial test, the hair treatment cream was well spreadable in hair and had no sticky feel.

TABLE 22

| | |
|---|---|
| (Component 1) | |
| Liquid paraffin | 9.0 |
| Cetyl octanoate | 4.0 |
| TTMMA-6 (Example 20) | 4.0 |
| Cetosteary alcohol | 3.0 |
| Cetanol | 2.0 |
| Propylene glycol stearate | 2.0 |
| Glyceryl stearate | 1.0 |
| Polyethylene glycol stearate | 1.0 |
| Distearyldimethylammonium chloride | 2.0 |
| (Component 2) | |
| N-coconut oil fatty acid-acyl-L-arginine ethyl ester DL- pyrrolidonecarboxylate | 0.5 |
| 1,3 -Butylene glycol | 5.0 |
| Chitin (aqueous 1% solution) | 10.0 |
| Perfume | ad lib. |
| Preservative | ad lib. |
| Pure water | balance |
| Total | 100% |

EXAMPLE 68

Hair Lotion

A hair lotion having the composition shown in Table 23 below was formulated in the following manner. I.e., the ingredients under Components 1 and 2 were separately heated to 80° C., and the ingredients under Component 1 were gradually added to the ingredients under Component 2 being stirred. The resulting mass was cooled to obtain a product of hair lotion. In its orisensual test, the hair lotion was well spreadable in hair and had no sticky feel.

TABLE 23

| | |
|---|---|
| (Component 1) | |
| Liquid paraffin | 15.0 |
| Vaseline | 5.0 |
| MMMA-10 (Example 1) | 10.0 |
| Isopropyl myristate | 10.0 |
| Bees wax | 1.0 |
| Stearic acid | 1.0 |
| Propylene glycol stearate | 1.0 |
| Polyethylene glycol stearate | 1.0 |
| Diglyceryl oleate | 4.0 |
| Hydrogenated soybean lecithin | 1.0 |
| (Component 2) | |
| Sodium N-stearoylglutamate | 0.4 |
| Xanthane gum (aqueous 1% solution) | 5.0 |
| Carboxyvinyl polymer (aqueous 1% solution) | 5.0 |
| Sodium polyaspartate solution (30%) | 1.0 |
| 1,3-Butylene glycol | 5.0 |
| Perfume | ad lib. |
| Preservative | ad lib. |
| Pure water | balance |
| Total | 100% |

EXAMPLE 69

Cleansing Foam

A cleansing foam having the composition shown in Table 24 below was formulated in the following manner. I.e., the ingredients under Components 1 and 2 were separately heated to 80° C., and the ingredients under Component 1 were gradually added to the ingredients under Component 2 being stirred. The resulting mass was cooled to obtain a product of cleansing foam. In its sensorial test, the cleansing foam was well spreadable on the skin and had a good refreshing feel with no stickiness.

TABLE 24

| | |
|---|---|
| (Component 1) | |
| TCAA-4 (Example 15) | 4.0 |
| Lauric acid | 3.0 |
| Myristic acid | 3.0 |
| Polyoxyethylene hardened castor oil | 2.0 |
| Coconut oil fatty acid diethanolamide | 8.0 |
| (Component 2) | |
| Sodium hydroxide | 0.5 |
| Arginine | 0.5 |
| Polyethylene glycol | 15.0 |
| Propylene glycol | 15.0 |
| Potassium N-myristoylglutamate | 15.0 |
| Sodium N-myristoylglutamate | 7.5 |
| Sodium N-lauroylglutamate | 7.5 |
| Perfume | ad lib. |
| Preservative | ad lib. |
| Pure water | balance |
| Total | 100% |

EXAMPLE 70

A cleansing oil having the composition shown in Table 25 below was formulated in an ordinary manner. In its sensorial test, the cleansing oil had a good refreshing feel with no stickiness, and was very good.

TABLE 25

| | |
|---|---|
| Liquid paraffin | 38.0 |
| MCAA-6 (Example 25) | 9.0 |
| MSAA-6 (Example 29) | 4.0 |
| 2-Ethylhexyl stearate | 20.0 |
| Dimethylpolysiloxane | 20.0 |
| POE(10) oleyl alcohol ether | 8.0 |
| Perfume | ad lib. |
| Preservative | ad lib. |
| Total | 100% |

EXAMPLE 71

Make-Up Remover

A make-up remover having the composition shown in Table 26 below was formulated in the following manner. I.e., the ingredients under Components 1 and 2 were separately heated to 80° C., and the ingredients under Component 1 were gradually added to the ingredients under Component 2 being stirred. The resulting mass was cooled to obtain a product of make-up remover. In its sensorial test, the make-up remover was well spreadable on the skin and had a good refreshing feel with no stickiness.

TABLE 26

| | |
|---|---|
| (Component 1) | |
| MMMA-6 (Example 4) | 2.0 |
| DMMA-6 (Example 5) | 2.0 |
| Sodium N-stearoylglutamate | 1.5 |
| N-coconut fatty acid-acylglutamic acid triethanolamine (30%) | 20.0 |
| Myristic acid | 2.0 |
| Arginine | 0.5 |
| Lysine | 0.5 |
| Pure water | balance |
| Preservative | ad lib. |
| (Component 2) | |
| Isostearic acid | 8.5 |
| Liquid paraffin | 55.0 |
| Total | 100% |

EXAMPLE 72

Shaving Foam

A shaving foam having the composition shown in Table 27 below was formulated in the following manner. I.e., glycerin, triethanolamine and the compound of Example 28 were added to pure water and heated to 70° C. to prepare an aqueous phase. The other ingredients were dissolved by heating to prepare an oily phase. The oily phase was added to the aqueous phase for neutralization. The liquid stock thus prepared was put into foaming bottles, which were then fitted with a valve and charged with gas. In its sensorial test, the shaving foam thus produced had a good refreshing feel with no stickiness.

TABLE 27

| | |
|---|---|
| (Liquid Stock) | |
| Stearic acid | 4.5 |
| Coconut oil fatty acid | 1.5 |
| Glycerol monostearate | 5.0 |
| Glycerin | 10.0 |

TABLE 27-continued

| | |
|---|---|
| MLγA-4 (Example 28) | 2.0 |
| Triethanolamine | 4.0 |
| Perfume | ad lib. |
| Pure water | balance |
| (For bottle charging) | |
| Liquid stock | 96 |
| LPG | 4 |
| Total | 100% |

EXAMPLE 73

Body Shampoo

A body shampoo having the composition shown in Table 28 below was formulated in an ordinary manner. In its sensorial test, the body shampoo gave a good refreshing feel to the skin having been shampooed with it, and had no sticky feel.

TABLE 28

| | |
|---|---|
| N-lauroylglutamic acid triethanolamine (30%) | 20.0 |
| N-Lauroylmethyltaurine sodium salt (30%) | 5.0 |
| Coconut oil fatty acid-acylglycine potassium salt (30%) | 5.0 |
| Lauric acid triethanolamine solution | 10.0 |
| Myristic acid triethanolamine solution | 10.0 |
| 2 Lauryl-N-carboxymethyl-N-hydroxyethyl imidazolinium betaine | 5.0 |
| Lauryldiethanolamide | 5.0 |
| Propylene glycol | 5.0 |
| DCGA-4 (Example 17) | 2.0 |
| Perfume | ad lib. |
| Dye | ad lib. |
| Preservative | ad lib. |
| Metal ion scavenger | ad lib. |
| Pure water | balance |
| Total | 100% |

The following Examples are to demonstrate the formulation of the percutaneous preparations of the present invention, in which the amount of each ingredient is in terms of % by weight.

EXAMPLE 74

Chloramphenicol Ointment

Chloramphenicol ointment having the composition shown in Table 29 below was formulated in an ordinary manner. In its sensorial test, the chloramphenicol ointment had good compatibility with the skin with no stickiness.

TABLE 29

| | |
|---|---|
| Chloramphenicol | 1.0 |
| Propylene glycol | 12.0 |
| Cetanol | 20.0 |
| Vaseline | 25.0 |
| MCAA-6 (Example 25) | 5.0 |
| Preservative | ad lib. |
| Pure water | balance |
| Total | 100% |

EXAMPLE 75

Adrenocortical Hormone Ointment

An adrenocortical ointment having the composition shown in Table 30 below was formulated in an ordinary manner. In its sensorial test, the adrenocortical hormone ointment had good compatibility with the skin with no stickiness.

TABLE 30

| | |
|---|---|
| Hydrocortisone acetate | 1.0 |
| Fradiomycin sulfate | 0.2 |
| Vaseline | 17.0 |
| TTCAA-6 (Example 13) | 5.0 |
| Liquid paraffin | 10.0 |
| Bleached bees wax | 5.0 |
| Stearyl alcohol | 10.0 |
| Glycerin | 12.0 |
| Sodium N-coconut oil fatty acid-acylglutamate | 1.0 |
| Preservative | ad lib. |
| Pure water | balance |
| Total | 100% |

As has been described in detail hereinabove, the N-long chain acyl-neutral amino acid polyglycerin ester composed of a polyglycerin having a degree of glycerin polymerization of not smaller than 4 and an N-long chain acyl-neutral amino acid having an acyl group with from 6 to 22 carbon atoms, and the nonionic surfactant composition comprising, as the active ingredient, at least one kind of such polyglycerin ester is favorably safe. Cosmetic compositions and percutaneous preparations containing such polyglycerin ester or such composition can be sensorially good.

What is claimed is:

1. An N-long chain acyl-neutral amino acid polyglycerin ester represented by the following general formula (I):

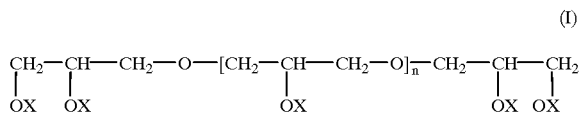

(I)

wherein n is at least 2, and

X is selected from the group consisting of:
  a hydrogen atom and
  an N-long chain acyl-neutral amino acid residue comprising an acyl group which contains 6 to 22 carbon atoms which may be straight- or branched-chained and saturated or unsaturated;

wherein at least one X is an N-long chain acyl-neutral amino acid residue comprising an acyl group which contains 6 to 22 carbon atoms which may be straight- or branched-chained and saturated or unsaturated, and wherein the degree of glycerin polymerization ranges from 4 to 10.

2. The N-long chain acyl neutral amino acid polyglycerin ester of claim 1, wherein n=2 and the degree of glycerin polymerization is 4.

3. The N-long chain acyl-neutral amino acid polyglycerin ester as claimed in claim 1, wherein said N-long chain acyl-neutral amino acid is an N-long chain acyl derivative of a neutral amino acid selected from the group consisting of glycine, alanine, β-alanine, α-aminobutyric acid, aminobutyric acid, sarcosine and N-methyl-β-alanine.

4. A nonionic surfactant composition comprising an effective amount of at least one kind of N-long chain acylneutral amino acid polyglycerin ester as set forth in claim 1.

5. A cosmetic composition comprising at least one kind of N-long chain acyl-neutral amino acid polyglycerin ester as set forth in claim 1 in an amount effective as a nonionic surfactant or emulsifier.

6. A percutaneous preparation comprising at least one kind of N-long chain acyl-neutral amino acid polyglycerin ester as set forth in claim 1 in an amount effective as a nonionic surfactant or emulsifier.

* * * * *